United States Patent [19]
Visentin et al.

[11] Patent Number: 5,480,880
[45] Date of Patent: Jan. 2, 1996

[54] PENEM DERIVATIVES

[75] Inventors: Giuseppina Visentin, Biassono; Franco Zarini, Settimo Milanese; Daniela Jabes, Milan; Ettore Perrone, Boffalora Ticino; Costantino della Bruna, Rho; Marco Alpegiani, Milan, all of Italy

[73] Assignee: Farmitalia Carlo Erba S.r.l., Milan, Italy

[21] Appl. No.: 972,444

[22] PCT Filed: Jun. 22, 1992

[86] PCT No.: PCT/EP92/01396

§ 371 Date: Apr. 9, 1993

§ 102(e) Date: Apr. 9, 1993

[87] PCT Pub. No.: WO93/00345

PCT Pub. Date: Jan. 7, 1993

[30] Foreign Application Priority Data

Jun. 21, 1991 [GB] United Kingdom ............ 9113427

[51] Int. Cl.⁶ .................... A61K 31/43; C07D 499/00
[52] U.S. Cl. .................................. 514/210; 540/310
[58] Field of Search ........................ 540/310; 514/210

[56] References Cited

FOREIGN PATENT DOCUMENTS 2072180  3/1990  Japan.

*Primary Examiner*—Richard D. Lovering
*Assistant Examiner*—Catherine S. Kilby Scalzo
*Attorney, Agent, or Firm*—Oblon, Spivak, McClelland, Maier & Neustadt

[57] ABSTRACT

The invention provides compounds of the general formula I

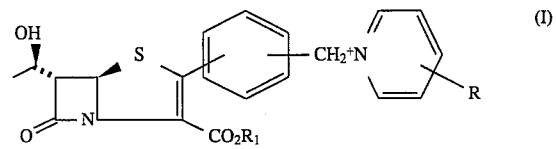

wherein $R_1$ is a hydrogen atom, a negative charge or an ester residue;

R is:
a) $—(CH_2)_n—A—CO_2H$, $—(CH_2)_n—A—SO_3H$ or $—(CH_2)_n—A—PO_3H_2$, wherein n is either zero, one or two and A is a group $—CH=CH—$ (either E or Z), $—OCH_2—$, $—SCH_2—$ or $—CHOH—$;
b) $—(CH_2)_n—PO_3H_2$, $—(CH_2)_nSO_2NHCN$, $—(CH_2)_nNHSO_3H$, $—(CH_2)_nCONHSO_2CH_3$ or $—(CH_2)_nCONHSO_2CF_3$, wherein n is as defined above;
c) $—(CH_2S)_m—W—(CH_2)_nZ$, wherein W is an arylene group or a heterocyclediyl group, m is 0 or 1, n is as above defined, and Z represents $CO_2H$, $PO_3H_2$, $SO_2NHCN$, $NHSO_3H$, $CONHSO_2CH_3$ or $CONHSO_2CF_3$;
d)

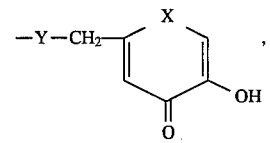

wherein Y is O or NH and X is NH, N—OH or N—O—$(CH_2)_{n+1}COOH$ wherein n is as defined above; or
e) $—(CH_2S)_m—W'$, wherein W' is a heterocyclyl group convertible into an anion at physiological pH and m is as defined above.

Compounds I, their salts and ester prodrugs have antibacterial activity.

5 Claims, No Drawings

PENEM DERIVATIVES

This application is a 371 of PCT/EP92/01396.

The present invention relates to penem compounds, to a process for their preparation, and to pharmaceutical and veterinary compositions containing them.

There is a continuing need for new antibiotics. Because of the confirmed wide scale use of known antibiotics, resistant strains of pathogens are selected. Accordingly, there is no constant effectiveness for any given antibiotic. Additionally, known antibiotics suffer from the disadvantage of being effective against only certain types of microorganisms, or they may produce undesired side-effects. There is thus a strongly felt need for new antibiotics which do not suffer from the above disadvantages.

Penem compounds are promising antibiotics, in particular the quaternary ammonium penems. In the past, several penem antibiotics featuring a quaternary ammonium at the C-2 sidechain have been investigated: E. Perrone et al., 2-(Quaternary ammonio)methyl penems, J. Antibiotics 39:1351 (1986): E. Perrone et al., Novel quaternary ammonium penems: the [(pyridino)methyl] phenyl derivatives, J. Antibiotics 40:1636 (1987); M. Alpegiani et al, 2-(Heteroatom-substituted)methyl penems. III. Nitrogen derivatives, Heterocycles 27:1329 (1988); G. Franceschi et al., 6-Hydroxyethyl penems—Ten years after, Recent Advances in the Chemistry of β-Lactam Antibiotics, P. H. Bently ed., The Royal Society of Chemistry, London 1989, p. 223–246. Unfortunately, these penems showed as unexpected side effect a high acute toxicity.

The present invention provides quaternary ammonium penems which did not display acute toxicity in mice up to the highest dose tested (2000–3000 mg/kg i.v.), and showed the following advantages:
(i) Stability towards renal dehydropeptidases;
(ii) Excellent efficacy against experimental infections in mice.

The compounds of the invention are quaternary ammonium penems of the following formula (I):

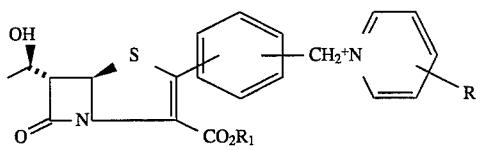

wherein $R_1$ is a hydrogen atom, a negative charge or an ester residue;
R is
a) $-(CH_2)_n A-CO_2H$ $-(CH_2)_n-A-SO_3H$, or $-(CH_2)_n-A-PO_3H_2$,
wherein n is either zero, one or two and A is a group $-CH=CH-$ (either E or Z), $-OCH_2-$, $-SCH_2-$ or $-CHOH-$;
b) $-(CH_2)_n-PO_3H_2$, $-(CH_2)_n SO_2 NHCN$, $-(CH_2)_n NHSO_3H$, $-(CH_2)_n CONHSO_2 CH_3$ or $-(CH_2)_n CONHSO_2 CF_3$, wherein n is as defined above;
c) $-(CH_2S)_m-W-(CH_2)_n Z$, wherein W is an arylene group or a heterocyclediyl group, m is 0 or 1, n is as above defined, and Z represents $CO_2H$, $PO_3H_2$, $SO_2NHCN$, $NHSO_3H$, $CONHSO_2CH_3$ or $CONHSO_2CF_3$;

d)

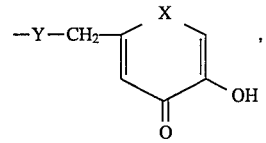

wherein Y is O or NH and X is NH, N—OH or N—O—$(CH_2)_{n+1}COOH$ wherein n is as defined above; or
e) $-(CH_2S)_m-W'$, wherein W' is a heterocyclyl group convertible into an anion at physiological pH and m is as defined above; and the pharmaceutically acceptable salts thereof.

The term arylene preferably encompasses a phenylene or naphthylene group.

A heterocyclediyl group is preferably an optionally substituted five- or six-membered unsaturated or saturated heterocyclic ring containing at least one nitrogen, oxygen or sulphur atom, and is more preferably a furanediyl, thiophenediyl, tetrazolediyl, thiazolediyl, isothiazolediyl, oxazolediyl, isoxazolediyl, thiadizaolediyl or a pyrrolediyl group.

A heterocyclyl group is preferably an optionally substituted five- or six-membered unsaturated or saturated heterocyclic ring containing at least one nitrogen, oxygen or sulphur atom. Preferred substituents are hydroxy, $C_1-C_4$ alkyl and an oxo group. More preferably, "heterocyclyl" represents a furanyl, thiophenyl, tetrazolyl, thiazolyl, isothiazolyl, oxazolyl, isoxazolyl, thiadiazolyl, pyrrolyl or triazinyl group, and most preferably a 2,5-dihydro-6-hydroxy- 2-methyl-5-oxo-1,2,4-triazin-3-yl group, a 2,5-dihyrdo- 6-hydroxy-4-methyl-5-oxo-1,2,4-triazin-3-yl group, or a 1,2,3,4-tetrazol-5-yl group.

Pharmaceutically or veterinarily acceptable salts of the compounds of formula I are included in the present invention. These salts may be prepared from the compounds of formula I and any pharmaceutically or veterinarily acceptable base. The last include either inorganic bases such as, e.g., alkali or alkaline-earth metal hydroxides, in particular sodium or potassium hydroxides, or organic bases, such as, e.g., triethylamine, including aminoacids such as lysine, procaine, arginine.

Preferred ester residues which $R_1$ may represent are those forming penem esters of the formula I which can be absorbed from the gastro-intestinal tract after oral administration, and then are hydrolyzed in the bloodstream by aspecific serum esterases, such as:
- acyloxymethyl or 3-(acyloxy)ethyl;
- benzoyloxymethyl or 3-(benzoyloxy)ethyl, either unsubstituted or substituted on the ring by a free, methylated or acetylated hydroxy or amino group;
- alkoxycarbonyloxymethyl or 3-(alkoxycarbonyloxy)ethyl;
- 3-phthalidyl;
- 2-oxo-3,3-dioxolan-4-yl, optionally substituted by a $C_1-C_4$ alkyl group in the 5 position;
- (2-oxo-1,3-dioxolen-4-yl)methyl, optionally substituted by a phenyl or $C_1-C_4$ alkyl group at the 5 position;
- a group $CH_2CO_2R'$, wherein R' is $C_1-C_4$ straight or branched alkyl, or benzyl; or
- 2-oxotetrahydrofuran-5-yl, optionally substituted by a $C_1-C_4$ alkyl group at the 4 position.

In the definition of $R_1$ above the term "acyl" is intended to include straight or branched $C_2-C_{10}$ alkanoyl or $C_4-C_8$ cycloalkanoyl groups.

More particularly preferred compounds are listed in Table 1.

TABLE 1

[Structure: penem compound with OH, S, CH₂⊕N-pyridinium-R, COO⊖ substituents]

| no. | isomer | R |
|---|---|---|
| 1 | meta | —CH₂SO₂NHCN |
| 2 | " | —SCH₂COOH |
| 3 | " | —OCH₂COOH |
| 4 | " | [CH=CH-CH₂COOH propenyl group] |
| 5 | " | [—O-CH₂-(N-hydroxy-4-oxo-5-hydroxy-pyridine)] |
| 6 | " | [—O-CH₂-(NH-4-oxo-5-hydroxy-pyridine)] |
| 7 | " | [—O-CH₂-(N-OCH₂COOH-4-oxo-5-hydroxy-pyridine)] |
| 8 | " | [—NH-CH₂-(N-OH-4-oxo-5-hydroxy-pyridine)] |
| 9 | " | [thiazine-CH₂-S- with COOH] |
| 10 | " | [—C₆H₄-COOH para] |
| 11 | " | [—C₆H₄-COOH meta] |

TABLE 1-continued

[Same penem structure]

| no. | isomer | R |
|---|---|---|
| 12 | " | [tetrazolyl-CH= with NH] |
| 13 | " | —CH(OH)SO₃H |
| 14 | para | —CH₂SO₂NHCN |
| 15 | " | —OCH₂COOH |
| 16 | " | —SCH₂COOH |
| 17 | " | —CH₂S—C(=N-tetrazole-CH₂COOH)— |
| 18 | " | [oxazole with COOH] |
| 19 | " | [CH=CH-CH₂COOH propenyl] |
| 20 | " | [pyrazole N—N / NH—N] |

The compounds of formula (I) can be prepared by a process comprising reacting a compound of formula (II), or a protected derivative thereof,

(II)

wherein R is as defined above, with a penem intermediate of formula (III)

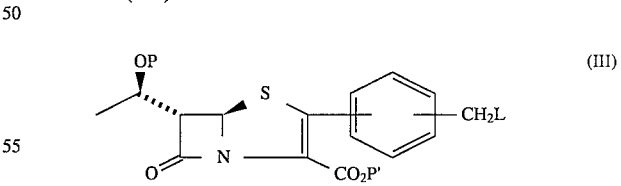

(III)

wherein P is either hydrogen or a hydroxy protecting group, P' is either R₁ or a carboxy protecting group, and L is a leaving group susceptible to nucleophilic displacement by the substituted pyridine of formula (II). The protecting groups optionally present, such as P and P' when they are not hydrogen, and others which may be desired to protect any function present in the group R of compound (II), are then removed and, if desired, the obtained compound is converted into a salt thereof with an organic or inorganic base.

The resulting compound may be converted optionally into an ester thereof by reaction with a suitable compound of the formula $R_1L$ wherein $R_1$ is an ester residue and L is as defined above after removal of the P' group.

The leaving group L may be, for example, a sulphonyloxy group —$OSO_2R'$, wherein R' is an unsubstituted or substituted alkyl group or an aryl group; or a halogen atom such as iodine, bromine or chlorine. A particularly preferred sulphonyloxy group is trifluoromethanesulphonyloxy, —$OSO_2CF_3$.

A carboxy protecting group P' may be any group which, together with the —$CO_2$— moiety, forms an esterified carboxy group. Examples of carboxy protecting groups are, in particular, $C_1$–$C_6$ alkyl groups, for instance methyl, ethyl or tert-butyl; halosubstituted $C_1$–$C_6$ alkyl groups, for example 2,2,2-trichloroethyl; $C_2$–$C_4$ alkenyl groups, for example allyl; unsubstituted or substituted aryl groups, for example phenyl and p-nitrophenyl; unsubstituted or substituted aryl $C_1$–$C_6$ alkyl groups, for example benzyl, p-nitrobenzyl and p-methoxy-benzyl; aryloxy-$C_1$–$C_6$ alkyl groups, for example phenoxy-ethyl; or groups such as benzhydryl, o-nitro-benzhydryl, acetonyl, trimethylsilyl, diphenyl-tert-butyl-silyl, and dimethyl-tert-butyl-silyl, or groups such as plvaloyloxy methyl or phthalidyl.

Particularly preferred carboxy protecting groups are allyl, p-nitrobenzyl, trimethylsilyl, dimethyl-tert-butyl-silyl, and trichloroethyl.

Particularly preferred hydroxy protecting groups P are trimethylsilyl, tert-butyldimethylsilyl, or carbonates, such as p-nitrobenzyl oxycarbonyl, allyloxycarbonyl and tetrahydropyranyl. The reaction between a compound of formula (II) and a compound of formula (III), may be performed in a suitable organic, preferably aprotic, solvent. Such a solvent may be, for instance, tetrahydrofuran, dimethylformamide, acetone or a halogenated hydrocarbon such as, e.g. ,. dichloromethane. The reaction temperature may, preferably, vary between about $-100°$ C. and about $+60°$ C., preferably between $-70°$ C. and $+45°$ C. When a compound of formula (II) is reacted with a compound of formula (III) wherein L is halogen, the presence of a silver salt, particularly if it is soluble in the media, e.g. $AgClO_4$ end $AgOSO_2CF_3$ may be beneficial.

Removal of the protecting groups can be effected by known per se procedures; e.g., silyl groups can be removed under mild acidic conditions, or by fluoride ions, e.g., with tetrabutylammonium fluoride; p-nitrobenzyl groups can be removed by reduction, e.g., by catalytic hydrogenation, or with metals, such as Fe and Zn; allyl carboxylates can be cleaved by transallylation with an organic acid or a salt thereof, such as acetic acid, 2-ethylhexanoic acid or their sodium and potassium salts, this reaction being catalyzed by a triphenylphosphine-palladium complex, preferably by tetrakis-triphenylphosphine-Pd(O).

The optional salification of an obtained compound and the reaction with the compound of the formula $R_1L$ as above defined for the ester formation may be carried out following known and conventional procedures.

The penem intermediates of formula (III) are known compounds described in our U.S. Pat. No. 4,863,914 (Sep. 5, 1989).

The substituted pyridines of formula (II) and the compounds $R_1L$ are known compounds or can be prepared from known compounds according to conventional methods.

The compounds of formula (I) provided by the present invention are potent, broad-spectrum, non-toxic antibacterial agents. In comparison to most penem antibiotics not bearing a quaternary ammonium group, they showed increased activity against experimental infections induced in mice by both Gram-positive and Gram-negative pathogens. In comparison to other quaternary ammonium compounds, they proved non-toxic. Table 2 shows in vivo data obtained for representative compound , described in Example 1 and having an acute toxicity greater than 3000 mg/Kg I.D. in the mouse.

TABLE 2

In vivo activity of Compound of formula (I), R = $CH_2SO_2NHCN$ (Example 1), in comparison with FCE 22101*, on mouse[a] systemic infections.

| Infection[c] | Treatment[d] | $ED_{50}$ (mg/kg)[b] | |
| --- | --- | --- | --- |
| | | Example 1 | FCE 22101 |
| S. aureus | 120 min | 0.16 | 0.70 |
| E. coli | 30–90–360 min | 0.65 | 10 |
| S. faecalis | 60–180 min | 8.50 | 80 |

[a] Female mice CD1 (Charles River, Italy), weighing 22 ± 2 g were used, experimentally infected by an introperitoneal route. Eight animals were used at each of the concentrations of compound tested, which were administered subcutaneously (0.1 ml/10 g weight). The mortality was recorded daily and the number of animals surviving on day 5 was used to calculate the cumulative effective dose ($ED_{50}$).
[b] Cumulative subcutaneous dose.
[c] Infecting organisms were: S. aureus, Staphylococcus aureus Smith ATCC 13709; E. Coli, Escherichia coli G (clinical isolate); S. faecalis, Streptococcus faecalis 3817 (clinical isolate).
[d] Minutes after infection.
*FCE 22101, one of the most advanced penems currently undergoing clinical evaluation (Journal of Antimicrobial Therapy, Supplement C to Volume 23, 1989, pp. 1–208), was taken as a significant reference compound of the prior art.

Because of their high antibacterial activity, the compounds of the invention are useful, for example, in the treatment of respiratory tract infections, for example, bronchitis, bronchopneumonia or pleuritis; hepatobiliary and abdominal infections; septicemia; urinary tract infections, for example, pyelonephritis or cystitis; obstetrical and gynecological infections, for instance, cervicitis or endometritis; ear, nose and throat infections, for instance otitis, sinusitis or parotitis. The compounds of the invention may be administered, either to humans or to animals, in a variety of dosage forms, e.g., orally in the form of tablets, capsules, drops or syrups; rectally in the form of suppositories; parenterally, e.g., intravenously or intramuscularly (as solutions or suspensions). Intravenous administration being preferred in emergency situations; by inhalation in the form of aerosols or solutions for nebulizers; intravaginally in the form, e.g., of bougies; or topically in the form of lotions, creams and ointments. The pharmaceutical or veterinary compositions containing the compounds of formula (I), which are also within the scope of the invention, may be prepared in a conventional way by employing the conventional carriers or diluents used for e.g., cephalosporins, Conventional carriers or diluents are, for example, water, gelatine, lactose, starches, magnesium stearate, talc, vegetable oils, cellulose and the like, Daily doses in the range of about 0.5 to about 100 mg per kg of body weight may be used, in various animal species. The exact dose depends on the age, weight and condition of the subject to be treated and on the frequency and route of administration.

A preferred way of administration of the compound of the invention is parenteral administration. In this case the compounds may be administered, for example to adult humans, in an amount ranging from about 250 mg to about 1000 mg per dose, preferably about 500 mg per dose, 1–4 times a day, dissolved in a suitable solvent such as, for example, sterile water of lidocaine hydrochloride solution for intramuscular injections, and sterile water, physiological saline solution, dextrose solution or the conventional intravenous fluids or electrolytes, for intravenous injections. Furthermore, the compounds of the invention may be used as antibacterial agents in a prophylactic manner, e.g., in cleaning or as surface disinfecting compositions, for example, at a concentration of about 0.2 to 1% by weight of such compounds admixed with, suspended, or dissolved in conventional inert dry or aqueous carriers for application by washing or spraying. They are also useful as nutritional supplements in animal feeds. Other features of the invention will be apparent in the course of the following descriptions of exemplary embodiments which are given for illustration of the invention and are not intended to be limiting thereof.

EXAMPLE (5R,6S)-6-/1 (R)-Hydroxyethyl/-2-/4-/4-(N-cyanosulfamoylato) methyl-1-pyridinio/methylphenyl/penem-3-carboxylic acid.

N-ethyldiisopropylamine (260 µl) was added to a mixture of allyl (5R, 6S )-6-/1(R)hydroxyethyl/-2-/4-(bromomethyl)phenyl/penem- 3-carboxylate (750 mg) and N-cyano-4 pyridylmethane-sulphonamide (300 mg) in dry DMF (3 ml).

The solution was stirred at r.t. for 10 hours. $Et_2O$ ( 50 ml ) was added dropwise. A gummy solid was isolated which on grinding under fresh $Et_2O$ produced a fine yellow powder (712 mg).

$^1$H-NMR(200 $MH_z$, DMSO-$d_6$):
1.20 (d, J=6.8 Hz, 3H )
3.90 (dd, J=1.6,5.9 Hz, 1H)
4.00 ($dd_q$, J=5.9,4.6,6.8 Hz, 1H)
4.50 (m, 2H)
4.56 (s,2H)
5.06 (m,2H)
5.24 (d, J=4.6 Hz, 1H)
5.69 (m, 1H)
5.78 (d,J=1.6 Hz)
5.84 (s,2H)
7.50 (s,4H)
8.13 (d, J=6.7 Hz, 2H)
9.14 (d, J=6.7 Hz, 2H)

This material was dissolved in THF(18 ml),$CH_2Cl_2$(18 ml), $CH_3CN$(24 ml) and HOAc(2.3 ml). The mixture was stirred under argon in the presence of $PPh_3$(75 mg) and $Pd(PPh_3)_4$(75 mg). Another equivalent quantity of catalyst was added after 30' and the suspension was stirred until the reaction was judged complete by TLC.

$Et_2O$ was added and the solid collected by centrifugation was dissolved in water/acetone 90/10 and purified by reverse-phase chromatography (LiChroprep RP-18 Merck, water/acetone—90/10 as eluent ). The appropriate fractions were combined and freeze-dried to afford the title compound (310 mg).

$^1$H-NMR(200MHz, DMSO-$d_6$):
1.15 (d,J=6.8 Hz,3H)
3.65 (dd,J=1.6,6.4 Hz, 1H)
3.93 ($dd_q$;J=6.4,5.3,6.8 Hz,1H)
4.54 (s, 2H)
5.15 (d, J=5.3 Hz, 1H)
5.58 (d, J=1.6 Hz, ]H)
5.80 (s,2H)
7.47 (m,4H)
8.10 (d, J=6.8Hz, 2H)
9.12 (d, J=6.8Hz, 2H)
U.V: λ max ($H_2O$, $NaHCO_3$ 1eq) 330 nm.

EXAMPLE 2

(5R, 6S)-6-/1(R)-hydroxyethyl/-2-/4-(3-(2-carboxylato ethenyl)pyridinio)methylphenyl)penem-3-carboxylic acid.

Trans-3-pyridylacrylic acid (950 mg) in MeOH (70 ml) was treated portionwise with KOMe (445 mg).

The solution was stirred at r.t. for 20' then concentrated under vacuum. Acetone was added to the residue and the solid filtered off to give the potassium salt of trans-3-pyridylacrylic acid.

The above salt (200 mg) in DMF (9 ml ) was treated with allylbromide (100 µl). The solution was stirred at r.t. for 16h then concentrated under vacuum. The resulting mixture was partitioned between $H_2O$ and $CH_2Cl_2$. The organic layer was separated, washed with $H_2O$ (4 times), dried and evaporated to give the allyl ester of trans-3-pyridylacrylic acid as an oil (150 mg).

The above crude material was dissolved in DMF (0.2 ml) and added to a solution of allyl (5R,6S)-6-/1(R)hydroxyethyl/-2-/ 4-(bromomethyl)phenyl/penem-3-carboxylate (230 mg) in DMF (0.6 ml). The solution was stirred at r.t. for 5h then $Et_2O$ was added. A rubbery solid separated which was washed with $Et_2O$ (3 times) and stripped at the vacuum pump. The resulting residue was dissolved in $CH_3CN$(10 ml), HOAc(3 ml), THF(8 ml), $CH_2Cl_2$(8 ml) and stirred under argon in the presence of $PPh_3$ and $Pd(PPh_3)_4$ (60 mg each)

After 1h the addition of $PPh_3$ and $Pd(PPh_3)_4$ was repeated and stirring was continued for one additional hour (TLC monitoring). $Et_2O$ was added dropwise and the crude solid collected after centrifugation was dissolved in water/acetone 90/10 and purified by reverse-phase chromatography (LiChoprep RP-18, water/acetone 90/10 as eluant). Freeze-drying of the proper fractions afforded the title compound (100 mg).

$^1$H-NMR (200$MH_z$, DMSO-$d_6$ ):
1.15 (d, J=6.4 Hz, 3H)
3.62 (dd,J=1.7,6.7 Hz, 1H)
3.93 (d, J=6.7,6.4 Hz, 1H)
5.59 (d,J=1.7 Hz, 1H)
5.79 (s,2H)
6.85 (d, J=16.0 Hz, 1H)
7.50 (m,4H)
7.53 (d,J=16.0 Hz, 1H)
8.12 (dd,J=6.2,8.0Hz, 1H)
8.80 (d, J=8.0 Hz, 1H)
9.08 (d, J=6.2 Hz, 1H)
9.38 (s,1H)
IR (KBr): ν max 3000–3700, 1770, 1580 $cm^{-1}$.

EXAMPLE 3

(5R, 6S ) -6-/1(R) hydroxyethyl/-2-/4- (4-carboxylatomethylthio- 1-pyridinio)methylphenyl/penem-3-carboxylic acid.

4-Pyridylthioacetic acid (3.38 g) , $NEt_3$ (3.06 ml) and allyl bromide (1.86 ml ) in DMF (110 ml ) were stirred at r. t. for 1 day. The solvent was concentrated under vacuum and the residue was partitioned between $H_2O$ and AcOET. The organic layer was washed in succession with $H_2O$, $NaHCO_3$acq, brine, then dried over $Na_2SO_4$ and concentrated under vacuum to afford the allyl ester of 4-pyridylthioacetic acid (1.23 g). The above crude ester (106 mg) in DMF (0.5 ml) was added to a solution of allyl (5R,6S)-6-/ l(R) hydroxyethyl/-2-/4-(bromomethyl)phenyl/penem-3-carboxylate (200 mg) in DMF (0.3 ml) and the solution was stirred at r.t. for 3 h. The solvent was stripped at the vacuum pump. The residue was dissolved in the minimum Quantity of acetone and AcOEt was added to separate an oil which was washed with AcOEt (2 times) and then stripped at the mechanical pump to afford a dark yellow foam ( 190 mg) .
$^1$H-NMR( 200 MH$_z$, Acetone d$_6$):
1.29 (d,J=6.4 Hz, 3H)
3.88 (dd,J=1.6,6.9Hz, 1H)
4.18 (m, 1H)
4.44 (s,2H
4.5–4.7 (m,4H.
4.81 (d,J=5.1Hz, 1H)
5.0–5.4 (m, 4H )
5.7–6.0 (m, 2H)
5.97 (d, J=1.6 Hz)
6.10 (s,2H)
7.5–7.7 (m,4H)
8.09 (d, J=7.2 Hz, 2H)
9.23 (d, J=7.2 Hz, 2H)

The above solid foam (185 was dissolved in a solution of CH$_3$CN (10 ml), HOAc (2.5 ml) THF (10 ml), CH$_2$Cl$_2$ (10 ml). The mixture was stirred under argon in the presence of PPh$_3$ (100 mg) and Pd (PPh$_3$)$_4$ (100 mg) for 30 monitoring the reaction by TLC. Et$_2$O was added to complete the precipitation of a solid which was recovered by centrifugation. The crude product was purified by reverse-phase chromatography (LiChroprep RP-18 Merck, water and water/acetone gradient as eluants). Freeze-drying of the collected fractions containing the product afforded the title compound (80 mg).
$^1$H-NMR(200MH$_z$, DMSO-d$_6$):
1.15 (d, J=6.3 Hz ,3H)
3.74 (dd, J=1.6,6.3 Hz, 1H)
3.84 (s,2H)
3.95 (d$_q$,J=6.3,6.3 Hz, 1H)
5.61 (s,2H)
5.66 (d, J=1.6 Hz, 1H)
7.43 (m,4H)
7.84 (d,J=6.8 Hz,2H)
8.75 (d,J=6.8 Hz,2H)
IR ν $_{max}$(KBr) 3000–3700, 1775, 1625, cm$^{-1}$
U.V. λ $_{max}$(H$_2$O) 310 nm.

EXAMPLE 4

(5R, 6S)-6-[1(R) hydroxyethyl]-2-{4-[3-(carboxylatomethoxy)-1-pyridino] methylphenyl}penem-3-carboxylic acid.

A solution of allyl (5R, 6S)-6-[1(R)hydroxyethyl]-2-[4-(bromomethyl)phenyl] penem-3-carboxylate (700 mg) in anhydrous DMF (5 ml) was treated with 3-(allyloxycarbonylmethoxy)pyridine (360 mg) and stirred at room temperature for 22 h. The reaction mixture was partitioned between EtOAc and water. The aqueous phase was washed with dichloromethane then evaporated to dryness under vacuum. The oily residue (1.15 g) was dissolved in CH$_3$CN/ CH$_3$COOH 10:1 (30 ml) and the resulting solution was treated with PPh$_3$ (300 mg) and Pd(PPh$_3$)$_4$ (300 mg) and stirred for two hours.

Acetonitrile (20 ml) was added and the precipitate was filtered, dissolved in the minimum amount of water and purified by reverse-phase chromatography (Lichroprep RP-18 Merck®, water/acetone mixtures as eluants). The product containing fractions were freeze-dried to afford the title compound (300 mg).
UV (H$_2$O) λ max 330 nm (ε=6110)
PMR (200 MHZ, D$_2$O)
1.30(d, J=6.3 Hz, 3H)
4.01(d, J=5.8 Hz, 1H)
4.25(dq, J=5.8, 6.3 Hz 1H )
4.70(s, 2H)
5.78(s, 2H)
7.46, 7.50(two d, J=8.2 Hz, 2H )
7.8–8.2(m, 2H)
8.49(d, J=5.8 Hz, 1H)
8.60(s, 1 H)

EXAMPLE 5

Operating as described in the previous examples, the following compounds were analogously prepared:
- (5R, 6S)-6-[1(R)- hydroxyethyl]-2-[3-(4-carboxylato-1,3-thiazol- 2-yl)-1-pyridinio]methylphenyl]penem-3-carboxylic acid;
- (5R, 6S )-6-[1 (R)-hydroxyethyl]-2- [4-( 4-carboxylato-1,3-oxazol- 5-yl )-1-pyridinio]methylphenyl]penem-3-carboxylic acid;
- (5R, 6S)-6-[1(R)-hydroxyethyl]-2-[3-(1-H-1,2,3,4-tetrazol- 5-yl)-1-pyridinio]methylphenyl]penem-3-carboxylic acid;
- (5R, 6S)-6-[1(R)-hydroxyethyl]-2-[4-(1-H-1,2,3,4-tetrazol- 5-yl )-1-pyridinio]methylphenyl]penem-3-carboxylic acid.

We claim:
1. A compound of the following formula I:

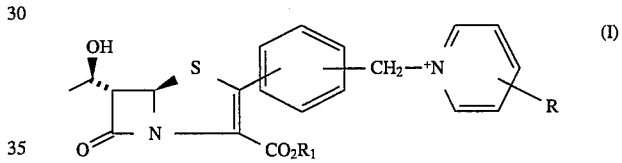

wherein R$_1$ is a hydrogen atom, a negative charge or an ester residue selected from the group consisting of: acyloxymethyl and 1-(acyloxy)ethyl, wherein the acyl moiety is selected from the group consisting of straight and branched C$_2$-C$_{10}$ alkanoyl and C$_4$-C$_8$ cycloalkanoyl groups;
benzoyloxymethyl and 1- (benzoyloxy) ethyl, either unsubstituted or substituted on the ring by a free, methylated or acetylated hydroxy or amino group;
alkoxycarbonyloxymethyl and 1- (alkoxycarbonyloxy) ethyl;
3-phthalidyl;
2-oxo-1,3-dioxolan-4-yl, optionally substituted at position 5 by a C$_1$-C$_4$ alkyl group;
(2-oxo-1,3-dioxolen-4-yl) methyl, optionally substituted at position 5 by a phenyl or C$_1$-C$_4$ alkyl group;
a group —CH$_2$CO$_2$R' wherein R' is C$_1$-C$_4$ straight or branched alkyl, or benzyl; and
2-oxotetrahydrofuran-5-yl, optionally substituted at position 4 by a C$_1$-C$_4$ alkyl group;
R is:
(a) —(CH$_2$)$_n$—A—CO$_2$H, —(CH$_2$)$_n$—A—SO$_3$H or —(CH$_2$)$_n$—A—PO$_3$H$_2$, wherein n is either zero, one or two and A is a group —CH═CH— (either E or Z ), —OCH$_2$-, —SCH$_2$— or —CHOH—;
(b) —(CH$_2$)$_n$—PO$_3$H$_2$, —(CH$_2$)$_n$SO$_2$NHCN, —(CH$_2$)$_n$NHSO$_3$H, —(CH$_2$)$_n$CONHSO$_2$CH$_3$ or —(CH$_2$)$_n$—CONHSO$_2$CF$_3$, wherein n is as defined above;
(c) —(CH$_2$S)$_m$—W—(CH$_2$)$_n$Z, wherein W is an arylene group or a heterocyclediyl group selected from the group consisting of a furanediyl, thiophenediyl, tetrazolediyl, thiazolediyl, isothiazolediyl, oxazolediyl, isoxazolediyl, thiadiazolediyl and pyrrolediyl group, m is 0 or 1, n is as above defined, and Z represents $CO_2H$, $PO_3H_2$, $SO_2NHCN$, $NHSO_3H$, $CONHSO_2CH_3$ or $CONHSO_2CF_3$;

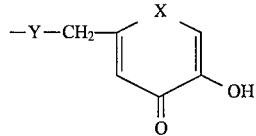

wherein Y is O or NH and X is NH, N—OH or N—O—$(CH_2)_{n+1}$ COOH wherein n is as defined as above; or (e) —$(CH_2S)_m$-W' wherein W' is a heterocyclyl group convertible into an anion at physiological pH and m is as defined above;

or when $R^1$ is other than a negative charge, a pharmaceutically acceptable salt thereof.

2. A compound of formula (I) or salt thereof according to claim 1 in which $R_1$ is a negative charge.

3. A compound of formula (I) or salt thereof according to claim 1 which is (5R,6S)-6-[1(R)Hydroxyethyl]- 2-[4-[4-(N-cyanosulfamoylato)methyl-1-pyridinio]-methylphenyl] penem-3-carboxylic acid or (5R,6S)-6-[ 1(R)hydroxyethyl] -2-{4-[3-(carboxylatomethoxy)-1-pyridinio] methylphenyl}penem-3-carboxylic acid.

4. A pharmaceutical composition comprising a pharmaceutically or veterinarily acceptable diluent or carrier and, as active principle, a compound of formula (I) as defined in claim 1 or a pharmaceutically or veterinarily acceptable salt or ester prodrug thereof.

5. A method of treating a patient with an antibacterial agent, which method comprises administering to the patient a therapeutically effective amount of a compound as defined in claim 1, or a pharmaceutically acceptable salt thereof.

* * * * *